US006287756B1

(12) United States Patent
Türeci et al.

(10) Patent No.: US 6,287,756 B1
(45) Date of Patent: Sep. 11, 2001

(54) METHODS FOR DETERMINING PRESENCE OF CANCER IN A SAMPLE BY DETERMINING EXPRESSION OF AN SSX GENE

(75) Inventors: Özlem Türeci, Homburg/Saar (DE); Yao-Tseng Chen, New York, NY (US); Ugur Sahin, Homburg/Saar (DE); Ali O. Gure; Lloyd J. Old, both of New York, NY (US); Michael Pfreundschuh, Homburg/Saar (DE)

(73) Assignee: Ludwig Institute for Cancer Research, New York, NY (US)

( * ) Notice: Subject to any disclaimer, the term of this patent is extended or adjusted under 35 U.S.C. 154(b) by 0 days.

(21) Appl. No.: 09/105,839

(22) Filed: Jun. 26, 1998

Related U.S. Application Data

(63) Continuation-in-part of application No. 08/851,130, filed on May 5, 1997, now Pat. No. 5,779,359.

(51) Int. Cl.$^7$ ............... G01N 33/53; G01N 33/574; G01N 33/48; C12P 19/34; C12Q 1/00
(52) U.S. Cl. ............... 435/4; 435/7.23; 435/91.2; 435/6; 435/7.1; 436/64
(58) Field of Search .............. 435/4, 6, 7.1, 7.23, 435/91.2; 436/64

(56) References Cited

U.S. PATENT DOCUMENTS 5,864,015 * 1/1999 Pfreundschuh ............... 530/350

FOREIGN PATENT DOCUMENTS

WO9602641A2 * 2/1996 (GB) .

OTHER PUBLICATIONS

Gure et al., SSSX: A multigene family with several members transcribed in normal testis and human cancer, International Journal of Cancer, 72, pp. 965–971, Oct. 15, 1996.*

Tureci et al., The new melanoma–associated antigen HOM–MEL–40 has a tyrosine kinase binding domain and is coded by the SSX gene which is involved in the t(11:X) translocation in chondrosarcoma, Proceedings of the American Association for Cancer Research, Mar. 1996.*

Heyting, et al, "Synaptonemal Complex Proteins," *Genome* 31:81–87 (1989).

Meuwissen, et al, "A coiled–coil related protein specific for synapsed regions of meiotic prophase chromosomes," *EMBO J* 11(13): 5091–5100 (1992).

Crew, et al, "Fusion of SYT to two genes, SSX1 and SSX2, encoding proteins with homology to the Kruppel associated box in human synovial sarcoma," *EMBO J* 14:2333–2340 (1995).

Sage, et al, "cDNA sequence of the murine synaptonemal complex protein 1 (SCP1)" *Biochim et. Biophysica Acta* 1258:258–260 (1995).

Tureci, et al, "The SSX–2 Gene, which Is Involved In The (tX: 18) Translocation of Synovial Sarcomas, Codes For the Human Tumor Antigen HOM–MEL–40," *Canc. Res.* 56:4766–4772 (1996).

Meuwissen, et al, "Human Synaptonemal Complex Protein 1 (SCP1): Isolation and Characterization of the cDNA and Chromosomal Localization of the Gene," *Genomics* 39.377–384 (1997).

Tureci, et al, "Identification of a meiosis specific protein as a member of the class of cancer/testis antigens," *Proc. Nate. Acad. Sci.* USA 95:5211–5216 (1998).

* cited by examiner

*Primary Examiner*—Anthony C. Caputa
*Assistant Examiner*—Jennifer Hunt
(74) *Attorney, Agent, or Firm*—Fulbright & Jaworski, LLP

(57) ABSTRACT

The invention relates to members of the SSX family of genes, as well as to their uses.

21 Claims, No Drawings

SEQUENCE LISTING

<160> NUMBER OF SEQ ID NOS: 72

<210> SEQ ID NO 1
<211> LENGTH: 766
<212> TYPE: DNA
<213> ORGANISM: Homo sapiens

<400> SEQUENCE: 1

-continued

| | |
|---|---|
| cactttgtca ccaactgctg ccaactcgcc accactgctg ccgcaatcgc aaccactgct | 60 |
| ttgtctctga agtgagactg ctcctggtgc catgaacgga gacgacacct ttgcaaagag | 120 |
| acccagggat gatgctaaag catcagagaa gagaagcaag gcctttgatg atattgccac | 180 |
| atacttctct aagaaagagt ggaaaaagat gaaatactcg gagaaaatca gctatgtgta | 240 |
| tatgaagaga aactataagg ccatgactaa actaggtttc aaagtcaccc tcccaccttt | 300 |
| catgtgtaat aaacaggcca cagacttcca ggggaatgat tttgataatg accataaccg | 360 |
| caggattcag gttgaacatc ctcagatgac tttcggcagg ctccacagaa tcatcccgaa | 420 |
| gatcatgccc aagaagccag cagaggacga aaatgattcg aagggagtgt cagaagcatc | 480 |
| tggcccacaa aacgatggga acaactgca ccccccagga aaagcaaata tttctgagaa | 540 |
| gattaataag agatctggac ccaaaagggg gaaacatgcc tggacccaca gactgcgtga | 600 |
| gagaaagcag ctggtgattt atgaagagat cagtgaccct gaggaagatg acgagtaact | 660 |
| cccctggggg atacgacaca tgcccttgat gagaagcaga acgtggtgac ctttcacgaa | 720 |
| catgggcatg gctgcggctc cctcgtcatc aggtgcatag caagtg | 766 |

<210> SEQ ID NO 2
<211> LENGTH: 931
<212> TYPE: DNA
<213> ORGANISM: Homo sapiens

<400> SEQUENCE: 2

| | |
|---|---|
| actttctctc tctttcgatt cttccatact cagagtacgc acggtctgat tttctctttg | 60 |
| gattcttcca aaatcagagt cagactgctc ccggtgccat gaacggagac gacgcctttg | 120 |
| caaggagacc cacggttggt gctcaaatac cagagaagat ccaaaaggcc ttcgatgata | 180 |
| ttgccaaata cttctctaag gaagagtggg aaaagatgaa agcctcggag aaaatcttct | 240 |
| atgtgtatat gaagagaaag tatgaggcta tgactaaact aggtttcaag gccaccctcc | 300 |
| cacctttcat gtgtaataaa cgggccgaag acttccaggg gaatgatttg gataatgacc | 360 |
| ctaaccgtgg gaatcaggtt gaacgtcctc agatgacttt cggcaggctc caggaatct | 420 |
| ccccgaagat catgcccaag aagccagcag aggaaggaaa tgattcggag gaagtgccag | 480 |
| aagcatctgg cccacaaaat gatgggaaag agctgtgccc ccgggaaaa ccaactacct | 540 |
| ctgagaagat tcacgagaga tctggaccca aaggggggga acatgcctgg acccacagac | 600 |
| tgcgtgagag aaaacagctg gtgatttatg aagagatcag cgaccctgag gaagatgacg | 660 |
| agtaactccc ctcagggata cgacacatgc ccatgatgag aagcagaacg tggtgacctt | 720 |
| tcacgaacat gggcatggct gcggacccct cgtcatcagg tgcatagcaa gtgaaagcaa | 780 |
| gtgttcacaa cagtgaaaag ttgagcgtca tttttcttag tgtgccaaga gttcgatgtt | 840 |
| agcgtttacg ttgtattttc ttacactgtg tcattctgtt agatactaac atttcattga | 900 |
| tgacgaagac atacttaatc gatatttggt t | 931 |

<210> SEQ ID NO 3
<211> LENGTH: 23
<212> TYPE: DNA
<213> ORGANISM: Homo sapiens

<400> SEQUENCE: 3

| | |
|---|---|
| cacacaggat ccatgaacgg aga | 23 |

<210> SEQ ID NO 4
<211> LENGTH: 33

```
<212> TYPE: DNA
<213> ORGANISM: Homo sapiens

<400> SEQUENCE: 4
cacacaaagc tttgagggga gttactcgtc atc                                  33

<210> SEQ ID NO 5
<211> LENGTH: 576
<212> TYPE: DNA
<213> ORGANISM: Homo sapiens

<400> SEQUENCE: 5
atgaacggag acgacgcctt tgcaaggaga cccagggatg atgctcaaat atcagagaag     60
ttacgaaagg ccttcgatga tattgccaaa tacttctcta agaaagagtg ggaaaagatg    120
aaatcctcgg agaaaatcgt ctatgtgtat atgaagctaa actatgaggt catgactaaa    180
ctaggtttca aggtcaccct cccacctttc atgcgtagta acgggctgc agacttccac     240 gggaatgatt ttggtaacga tcgaaaccac aggaatcagg ttgaacgtcc tcagatgact    300
ttcggcagcc tccagagaat cttcccgaag atcatgccca agaagccagc agaggaagaa    360
aatggtttga aggaagtgcc agaggcatct ggcccacaaa atgatgggaa acagctgtgc    420
cccccgggaa atccaagtac cttggagaag attaacaaga catctggacc caaaagggggg   480 aaacatgcct ggacccacag actgcgtgag agaaagcagc tggtggttta tgaagagatc    540
agcgaccctg aggaagatga cgagtaactc ccctcg                              576

<210> SEQ ID NO 6
<211> LENGTH: 576
<212> TYPE: DNA
<213> ORGANISM: Homo sapiens

<400> SEQUENCE: 6
atgaacggag acgacgcctt tgtacggaga cctagggttg gttctcaaat accacagaag     60
atgcaaaagg ccttcgatga tattgccaaa tacttctctg agaaagagtg ggaaaagatg    120
aaagcctcgg agaaaatcat ctatgtgtat atgaagagaa agtatgaggc catgactaaa    180
ctaggtttca aggccaccct cccacctttc atgcgtaata acgggtcgc agacttccag     240 gggaatgatt ttgataatga ccctaaccgt gggaatcagg ttgaacatcc tcagatgact    300
ttcggcaggc tccagggaat cttcccgaag atcacgcccg agaagccagc agaggaagga    360
aatgattcaa agggagtgcc agaagcatct ggcccacaga acaatgggaa acagctgcgc    420
ccctcaggaa aactaaatac ctctgagaag gttaacaaga catctggacc caaaagggggg   480 aaacatgcct ggacccacag agtgcgtgag agaaagcaac tggtggatta tgaagagatc    540
agcgaccctg cggaagatga cgagtaactc ccctca                              576

<210> SEQ ID NO 7
<211> LENGTH: 24
<212> TYPE: DNA
<213> ORGANISM: Homo sapiens

<400> SEQUENCE: 7
ctaaagccat gcagagaagg aagc                                           24

<210> SEQ ID NO 8
<211> LENGTH: 25
<212> TYPE: DNA
<213> ORGANISM: Homo sapiens
```

-continued

```
<400> SEQUENCE: 8
agatctctta ttaatcttc cagaaa                                         25

<210> SEQ ID NO 9
<211> LENGTH: 23
<212> TYPE: DNA
<213> ORGANISM: Homo sapiens

<400> SEQUENCE: 9
gtgctcaaat accagagaag atc                                           23

<210> SEQ ID NO 10
<211> LENGTH: 23
<212> TYPE: DNA
<213> ORGANISM: Homo sapiens

<400> SEQUENCE: 10
ttttgggtcc agatctcctc gtg                                           23

<210> SEQ ID NO 11
<211> LENGTH: 24
<212> TYPE: DNA
<213> ORGANISM: Homo sapiens

<400> SEQUENCE: 11
ggaagagtgg gaaaagatga aagt                                          24

<210> SEQ ID NO 12
<211> LENGTH: 22
<212> TYPE: DNA
<213> ORGANISM: Homo sapiens

<400> SEQUENCE: 12 cccctttttgg gtccagatat ca                                           22

<210> SEQ ID NO 13
<211> LENGTH: 25
<212> TYPE: DNA
<213> ORGANISM: Homo sapiens

<400> SEQUENCE: 13
aaatcgtcta tgtgtatatg aagct                                         25

<210> SEQ ID NO 14
<211> LENGTH: 22
<212> TYPE: DNA
<213> ORGANISM: Homo sapiens

<400> SEQUENCE: 14
gggtcgctga tctcttcata ac                                            22

<210> SEQ ID NO 15
<211> LENGTH: 23
<212> TYPE: DNA
<213> ORGANISM: Homo sapiens

<400> SEQUENCE: 15
gttctcaaat accagagaag atg                                           23

<210> SEQ ID NO 16
<211> LENGTH: 20
<212> TYPE: DNA
<213> ORGANISM: Homo sapiens
```

-continued

<400> SEQUENCE: 16
ctctgctggc ttctcgggcg                                              20

<210> SEQ ID NO 17
<211> LENGTH: 27
<212> TYPE: DNA
<213> ORGANISM: Homo sapiens

<400> SEQUENCE: 17
acagcattac caaggacagc agccacc                                      27

<210> SEQ ID NO 18
<211> LENGTH: 27
<212> TYPE: DNA
<213> ORGANISM: Homo sapiens

<400> SEQUENCE: 18
gccaacagca agatgcatac cagggac                                      27

<210> SEQ ID NO 19
<211> LENGTH: 9
<212> TYPE: PRT
<213> ORGANISM: Homo sapiens

<400> SEQUENCE: 19

Lys Ala Ser Glu Lys Ile Ile Tyr Val
1               5

<210> SEQ ID NO 20
<211> LENGTH: 10
<212> TYPE: PRT
<213> ORGANISM: Homo sapiens

<400> SEQUENCE: 20

Gly Ile Phe Pro Lys Ile Thr Pro Glu Lys
1               5                   10

<210> SEQ ID NO 21
<211> LENGTH: 10
<212> TYPE: PRT
<213> ORGANISM: Homo sapiens

<400> SEQUENCE: 21

Lys Leu Asn Thr Ser Glu Lys Val Asn Lys
1               5                   10

<210> SEQ ID NO 22
<211> LENGTH: 10
<212> TYPE: PRT
<213> ORGANISM: Homo sapiens

<400> SEQUENCE: 22

Lys Tyr Glu Ala Met Thr Lys Leu Gly Phe
1               5                   10

<210> SEQ ID NO 23
<211> LENGTH: 9
<212> TYPE: PRT
<213> ORGANISM: Homo sapiens

<400> SEQUENCE: 23

His Pro Gln Met Thr Phe Gly Arg Leu
1               5

<210> SEQ ID NO 24
<211> LENGTH: 9
<212> TYPE: PRT
<213> ORGANISM: Homo sapiens

<400> SEQUENCE: 24

Gly Pro Gln Asn Asn Gly Lys Gln Leu
1               5

<210> SEQ ID NO 25
<211> LENGTH: 8
<212> TYPE: PRT
<213> ORGANISM: Homo sapiens

<400> SEQUENCE: 25

Arg Val Arg Glu Arg Lys Gln Leu
1               5

<210> SEQ ID NO 26
<211> LENGTH: 9
<212> TYPE: PRT
<213> ORGANISM: Homo sapiens

<400> SEQUENCE: 26

Tyr Glu Ala Met Thr Lys Leu Gly Phe
1               5

<210> SEQ ID NO 27
<211> LENGTH: 9
<212> TYPE: PRT
<213> ORGANISM: Homo sapiens

<400> SEQUENCE: 27

Arg Glu Arg Lys Gln Leu Val Ile Tyr
1               5

<210> SEQ ID NO 28
<211> LENGTH: 9
<212> TYPE: PRT
<213> ORGANISM: Homo sapiens

<400> SEQUENCE: 28

Lys Gln Leu Val Ile Tyr Glu Glu Ile
1               5

<210> SEQ ID NO 29
<211> LENGTH: 10
<212> TYPE: PRT
<213> ORGANISM: Homo sapiens

<400> SEQUENCE: 29

Met Thr Phe Gly Arg Leu Gln Gly Ile Phe
1               5                   10

<210> SEQ ID NO 30
<211> LENGTH: 9
<212> TYPE: PRT
<213> ORGANISM: Homo sapiens

<400> SEQUENCE: 30

Lys Ser Ser Glu Lys Ile Val Tyr Val
1               5

```
<210> SEQ ID NO 31
<211> LENGTH: 9
<212> TYPE: PRT
<213> ORGANISM: Homo sapiens

<400> SEQUENCE: 31

Val Met Thr Lys Leu Gly Phe Lys Val
1               5

<210> SEQ ID NO 32
<211> LENGTH: 10
<212> TYPE: PRT
<213> ORGANISM: Homo sapiens

<400> SEQUENCE: 32

Tyr Val Tyr Met Lys Leu Asn Tyr Glu Val
1               5                   10

<210> SEQ ID NO 33
<211> LENGTH: 10
<212> TYPE: PRT
<213> ORGANISM: Homo sapiens

<400> SEQUENCE: 33

Lys Leu Asn Tyr Glu Val Met Thr Lys Leu
1               5                   10

<210> SEQ ID NO 34
<211> LENGTH: 9
<212> TYPE: PRT
<213> ORGANISM: Homo sapiens

<400> SEQUENCE: 34

Lys Leu Asn Tyr Glu Val Met Thr Lys
1               5

<210> SEQ ID NO 35
<211> LENGTH: 10
<212> TYPE: PRT
<213> ORGANISM: Homo sapiens

<400> SEQUENCE: 35

Asn Tyr Glu Val Met Thr Lys Leu Gly Phe
1               5                   10

<210> SEQ ID NO 36
<211> LENGTH: 9
<212> TYPE: PRT
<213> ORGANISM: Homo sapiens

<400> SEQUENCE: 36

Arg Pro Gln Met Thr Phe Gly Ser Leu
1               5

<210> SEQ ID NO 37
<211> LENGTH: 9
<212> TYPE: PRT
<213> ORGANISM: Homo sapiens

<400> SEQUENCE: 37

Lys Pro Ala Glu Glu Glu Asn Gly Leu
1               5

<210> SEQ ID NO 38
<211> LENGTH: 9
```

```
<212> TYPE: PRT
<213> ORGANISM: Homo sapiens

<400> SEQUENCE: 38

Gly Pro Gln Asn Asp Gly Lys Gln Leu
1               5

<210> SEQ ID NO 39
<211> LENGTH: 9
<212> TYPE: PRT
<213> ORGANISM: Homo sapiens

<400> SEQUENCE: 39

Cys Pro Pro Gly Asn Pro Ser Thr Leu
1               5

<210> SEQ ID NO 40
<211> LENGTH: 8
<212> TYPE: PRT
<213> ORGANISM: Homo sapiens

<400> SEQUENCE: 40

Arg Leu Arg Glu Arg Lys Gln Leu
1               5

<210> SEQ ID NO 41
<211> LENGTH: 8
<212> TYPE: PRT
<213> ORGANISM: Homo sapiens

<400> SEQUENCE: 41

Arg Pro Arg Asp Asp Ala Gln Ile
1               5

<210> SEQ ID NO 42
<211> LENGTH: 9
<212> TYPE: PRT
<213> ORGANISM: Homo sapiens

<400> SEQUENCE: 42

Lys Pro Ala Glu Glu Asn Gly Leu
1               5

<210> SEQ ID NO 43
<211> LENGTH: 9
<212> TYPE: PRT
<213> ORGANISM: Homo sapiens

<400> SEQUENCE: 43

Tyr Glu Val Met Thr Lys Leu Gly Phe
1               5

<210> SEQ ID NO 44
<211> LENGTH: 9
<212> TYPE: PRT
<213> ORGANISM: Homo sapiens

<400> SEQUENCE: 44

Arg Glu Arg Lys Gln Leu Val Val Tyr
1               5

<210> SEQ ID NO 45
<211> LENGTH: 9
<212> TYPE: PRT
<213> ORGANISM: Homo sapiens
```

```
<400> SEQUENCE: 45

Lys Gln Leu Val Val Tyr Glu Glu Ile
1               5

<210> SEQ ID NO 46
<211> LENGTH: 10
<212> TYPE: PRT
<213> ORGANISM: Homo sapiens

<400> SEQUENCE: 46

Met Thr Phe Gly Ser Leu Gln Arg Ile Phe
1               5                   10

<210> SEQ ID NO 47
<211> LENGTH: 9
<212> TYPE: PRT
<213> ORGANISM: Homo sapiens

<400> SEQUENCE: 47

Lys Ile Gln Lys Ala Phe Asp Asp Ile
1               5

<210> SEQ ID NO 48
<211> LENGTH: 9
<212> TYPE: PRT
<213> ORGANISM: Homo sapiens

<400> SEQUENCE: 48

Lys Ala Ser Glu Lys Ile Phe Tyr Val
1               5

<210> SEQ ID NO 49
<211> LENGTH: 9
<212> TYPE: PRT
<213> ORGANISM: Homo sapiens

<400> SEQUENCE: 49

Ala Met Thr Lys Leu Gly Phe Lys Ala
1               5

<210> SEQ ID NO 50
<211> LENGTH: 9
<212> TYPE: PRT
<213> ORGANISM: Homo sapiens

<400> SEQUENCE: 50

Arg Leu Gln Gly Ile Ser Pro Lys Ile
1               5

<210> SEQ ID NO 51
<211> LENGTH: 9
<212> TYPE: PRT
<213> ORGANISM: Homo sapiens

<400> SEQUENCE: 51

Arg Leu Arg Glu Arg Lys Gln Leu Val
1               5

<210> SEQ ID NO 52
<211> LENGTH: 9
<212> TYPE: PRT
<213> ORGANISM: Homo sapiens

<400> SEQUENCE: 52
```

Thr Leu Pro Pro Phe Met Cys Asn Lys
1               5

<210> SEQ ID NO 53
<211> LENGTH: 10
<212> TYPE: PRT
<213> ORGANISM: Homo sapiens

<400> SEQUENCE: 53

Lys Ile Phe Tyr Val Tyr Met Lys Arg Lys
1               5                   10

<210> SEQ ID NO 54
<211> LENGTH: 10
<212> TYPE: PRT
<213> ORGANISM: Homo sapiens

<400> SEQUENCE: 54

Lys Tyr Glu Ala Met Thr Lys Leu Gly Phe
1               5                   10

<210> SEQ ID NO 55
<211> LENGTH: 9
<212> TYPE: PRT
<213> ORGANISM: Homo sapiens

<400> SEQUENCE: 55

Arg Pro Gln Met Thr Phe Gly Arg Leu
1               5

<210> SEQ ID NO 56
<211> LENGTH: 9
<212> TYPE: PRT
<213> ORGANISM: Homo sapiens

<400> SEQUENCE: 56

Gly Pro Gln Asn Asp Gly Lys Glu Leu
1               5

<210> SEQ ID NO 57
<211> LENGTH: 8
<212> TYPE: PRT
<213> ORGANISM: Homo sapiens

<400> SEQUENCE: 57

Arg Leu Arg Glu Arg Lys Gln Leu
1               5

<210> SEQ ID NO 58
<211> LENGTH: 9
<212> TYPE: PRT
<213> ORGANISM: Homo sapiens

<400> SEQUENCE: 58

Phe Ser Lys Glu Glu Trp Glu Lys Met
1               5

<210> SEQ ID NO 59
<211> LENGTH: 9
<212> TYPE: PRT
<213> ORGANISM: Homo sapiens

<400> SEQUENCE: 59

Tyr Glu Ala Met Thr Lys Leu Gly Phe

-continued

```
1               5

<210> SEQ ID NO 60
<211> LENGTH: 9
<212> TYPE: PRT
<213> ORGANISM: Homo sapiens

<400> SEQUENCE: 60

Arg Glu Arg Lys Gln Leu Val Ile Tyr
1               5

<210> SEQ ID NO 61
<211> LENGTH: 9
<212> TYPE: PRT
<213> ORGANISM: Homo sapiens

<400> SEQUENCE: 61

Leu Gln Gly Ile Ser Pro Lys Ile Met
1               5

<210> SEQ ID NO 62
<211> LENGTH: 9
<212> TYPE: PRT
<213> ORGANISM: Homo sapiens

<400> SEQUENCE: 62

Lys Gln Leu Val Ile Tyr Glu Glu Ile
1               5

<210> SEQ ID NO 63
<211> LENGTH: 9
<212> TYPE: PRT
<213> ORGANISM: Homo sapiens

<400> SEQUENCE: 63

Ala Met Thr Lys Leu Gly Glu Lys Val
1               5

<210> SEQ ID NO 64
<211> LENGTH: 9
<212> TYPE: PRT
<213> ORGANISM: Homo sapiens

<400> SEQUENCE: 64

Ala Met Thr Lys Leu Gly Phe Lys Val
1               5

<210> SEQ ID NO 65
<211> LENGTH: 9
<212> TYPE: PRT
<213> ORGANISM: Homo sapiens

<400> SEQUENCE: 65

Thr Leu Pro Pro Phe Met Cys Asn Lys
1               5

<210> SEQ ID NO 66
<211> LENGTH: 10
<212> TYPE: PRT
<213> ORGANISM: Homo sapiens

<400> SEQUENCE: 66

Asn Tyr Lys Ala Met Thr Lys Leu Gly Phe
1               5                   10
```

```
<210> SEQ ID NO 67
<211> LENGTH: 9
<212> TYPE: PRT
<213> ORGANISM: Homo sapiens

<400> SEQUENCE: 67

His Pro Gln Met Thr Phe Gly Arg Leu
1               5

<210> SEQ ID NO 68
<211> LENGTH: 9
<212> TYPE: PRT
<213> ORGANISM: Homo sapiens

<400> SEQUENCE: 68

Gly Pro Gln Asn Asp Gly Lys Gln Leu
1               5

<210> SEQ ID NO 69
<211> LENGTH: 8
<212> TYPE: PRT
<213> ORGANISM: Homo sapiens

<400> SEQUENCE: 69

Arg Leu Arg Glu Arg Lys Gln Leu
1               5

<210> SEQ ID NO 70
<211> LENGTH: 9
<212> TYPE: PRT
<213> ORGANISM: Homo sapiens

<400> SEQUENCE: 70

Arg Glu Arg Lys Gln Leu Val Ile Tyr
1               5

<210> SEQ ID NO 71
<211> LENGTH: 9
<212> TYPE: PRT
<213> ORGANISM: Homo sapiens

<400> SEQUENCE: 71

Lys Gln Leu Val Ile Tyr Glu Glu Ile
1               5

<210> SEQ ID NO 72
<211> LENGTH: 10
<212> TYPE: PRT
<213> ORGANISM: Homo sapiens

<400> SEQUENCE: 72

Met Thr Phe Gly Arg Leu His Arg Ile Ile
1               5                   10
```

METHODS FOR DETERMINING PRESENCE OF CANCER IN A SAMPLE BY DETERMINING EXPRESSION OF AN SSX GENE

RELATED APPLICATION

This application is a continuation in part of application Ser. No. 08/851,130 filed on May 5, 1997, now U.S. Pat. No. 5,779,359, which is incorporated by reference.

FIELD OF THE INVENTION

This invention relates to the isolation and cloning of genes which are members of the "SSX" family, which is discussed herein, and the uses thereof, including determination of cancer.

BACKGROUND AND PRIOR ART

It is fairly well established that many pathological conditions, such as infections, cancer, autoimmune disorders, etc., are characterized by the inappropriate expression of certain molecules. These molecules thus serve as "markers" for a particular pathological or abnormal condition. Apart from their use as diagnostic "targets", i.e., materials to be identified to diagnose these abnormal conditions, the molecules serve as reagents which can be used to generate diagnostic and/or therapeutic agents. A by no means limiting example of this is the use of cancer markers to produce antibodies specific to a particular marker. Yet another non-limiting example is the use of a peptide which complexes with an MHC molecule, to generate cytolytic T cells against abnormal cells.

Preparation of such materials, of course, presupposes a source of the reagents used to generate these. Purification from cells is one laborious, far from sure method of doing so. Another preferred method is the isolation of nucleic acid molecules which encode a particular marker, followed by the use of the isolated encoding molecule to express the desired molecule.

To date, two strategies have been employed for the detection of such antigens in e.g., human tumors. These will be referred to as the genetic approach and the biochemical approach. The genetic approach is exemplified by, e.g., dePlaen et al., Proc. Natl. Sci. USA 85: 2275 (1988), incorporated by reference. In this approach, several hundred pools of plasmids of a cDNA library obtained from a tumor are transfected into recipient cells, such as COS cells, or into antigen-negative variants of tumor cell lines. Transfectants are screened for the expression of tumor antigens via their ability to provoke reactions by anti-tumor cytolytic T cell clones. The biochemical approach, exemplified by, e.g., Mandelboim, et al., Nature 369: 69 (1994) incorporated by reference, is based on acidic elution of peptides which have bound to MHC-class I molecules of tumor cells, followed by reversed-phase high performance liquid chromatography (HPLC). Antigenic peptides are identified after they bind to empty MHC-class I molecules of mutant cell lines, defective in antigen processing, and induce specific reactions with cytotoxic T-lymphocytes. These reactions include induction of CTL proliferation, TNF release, and lysis of target cells, measurable in an MTT assay, or a $^{51}$Cr release assay.

These two approaches to the molecular definition of antigens have the following disadvantages: first, they are enormously cumbersome, time-consuming and expensive; second, they depend on the establishment of cytotoxic T cell lines (CTLs) with predefined specificity; and third, their relevance in vivo for the course of the pathology of disease in question has not been proven, as the respective CTLs can be obtained not only from patients with the respective disease, but also from healthy individuals, depending on their T cell repertoire.

The problems inherent to the two known approaches for the identification and molecular definition of antigens is best demonstrated by the fact that both methods have, so far, succeeded in defining only very few new antigens in human tumors. See, e.g., van der Bruggen et al., Science 254: 1643–1647 (1991); Brichard et al., J. Exp. Med. 178: 489–495 (1993); Coulie, et al., J. Exp. Med. 180: 35–42 (1994); Kawakami, et al., Proc. Natl. Acad. Sci. USA 91: 3515–3519 (1994).

Further, the methodologies described rely on the availability of established, permanent cell lines of the cancer type under consideration. It is very difficult to establish cell lines from certain cancer types, as is shown by, e.g., Oettgen, et al., Immunol. Allerg. Clin. North. Am. 10: 607–637 (1990). It is also known that some epithelial cell type cancers are poorly susceptible to CTLs in vitro, precluding routine analysis. These problems have stimulated the art to develop additional methodologies for identifying cancer associated antigens.

One key methodology is described by Sahin, et al., Proc. Natl. Acad. Sci. USA 92: 11810–11913 (1995), incorporated by reference. Also, see allowed U.S. patent application Ser. No. 08/580,980, now U.S. Pat. No. 6,025,191, filed on Jan. 3, 1996, and U.S. Pat. No. 5,698,396. All three of these references are incorporated by reference. To summarize, the method involves the expression of cDNA libraries in a prokaryotic host. (The libraries are secured from a tumor sample). The expressed libraries are then immunoscreened with absorbed and diluted sera, in order to detect those antigens which elicit high titer humoral responses. This methodology is known as the SEREX method ("Serological identification of antigens by Recombinant Expression Cloning"). The methodology has been employed to confirm expression of previously identified tumor associated antigens, as well as to detect new ones. See the above referenced patent applications and Sahin, et al., supra, as well as Crew, et al., EMBO J 144: 2333–2340 (1995).

The SEREX methodology has been applied to esophageal cancer samples, an esophageal cancer associated antigen has now been identified, and its encoding nucleic acid molecule isolated and cloned, as per U.S. patent application Ser. No. 08/725,182, filed Oct. 3, 1996, incorporated by reference herein.

The relationship between some of the tumor associated genes and a triad of genes, known as the SSX genes, is under investigation. See Sahin, et al., supra; Tureci, et al., Cancer Res 56:4766–4772 (1996). One of these SSX genes, referred to as SSX2, was identified, at first, as one of two genes involved in a chromosomal translocation event (t(X; 18) (p11.2; q 11.2)), which is present in 70% of synovial sarcomas. See Clark, et al., Nature Genetics 7:502–508 (1994); Crew et al., EMBO J 14:2333–2340 (1995). It was later found to be expressed in a number of tumor cells, and is now considered to be a tumor associated antigen referred to as HOM-MEL-40 by Tureci, et al, supra. Its expression to date has been observed in cancer cells, and normal testis only. This parallels other members of the "CT" family of tumor antigens, since they are expressed only in cancer and testis cells. Crew et al. also isolated and cloned the SSX1 gene, which has 89% nucleotide sequence homology with SSX2. Sequence information for SSX1 and SSX2 is presented as SEQ ID NOS: 1 and 2 respectively. See Crew et al., supra. Additional work directed to the identification of SSX genes has resulted in the identification of SSX3, as is described by DeLeeuw, et al., Cytogenet. Genet 73:179–183 (1996). The fact that SSX presentation parallels other, CT antigens suggested to the inventors that other SSX genes might be isolated. The parent application, supra discloses this work, as does Gure, et al. *Int. J. Cancer* 72:965–971 (1997), incorporated by reference.

With respect to additional literature on the SSX family, most of it relates to SSX1. See PCT Application W/96 02641A2 to Cooper, et al, detailing work on the determination of synovial sarcoma via determination of SSX1 or SSX2. Also note DeLeeuw, et al. Hum. Mol. Genet 4(6) :1097–1099 (1995). also describing synovial sarcoma and SYT-SSX1 or SSX2 translocation. Also see Kawai, et al, N. Engl. J. Med 338(3):153–160 (1998); Noguchi, et al. Int. J. Cancer 72(6):995–1002 (1997), Hibshoosh, et al., Semin. Oncol 24(5):515–525 (1997), Shipley, et al., Am. J. Pathol. 148(2):559–567 (1996); Fligman, et al. Am. J. Pathol. 147 (6); 1592–1599 (1995). Also see Chand, et al., Genomics 30(3):545–552 (1995), Brett, et al., Hum. Mol Genet 6(9): 1559–1564 (1997), deBruyn, et al, Oncogene (1313) :643–648. The SSX3 gene is described by deLeeuw, et al, Cytogenet Cell Genet 73(3):179–1983 (1966).

Application of a modification of the SEREX technology described supra has been used, together with other techniques, to clone two, additional SSX genes, referred to as SSX4 and SSX5 hereafter, as well as an alternate splice variant of the SSX4 gene. Specifically, while the SEREX methodology utilizes autologous serum, the methods set forth infra use allogenic serum. This, as well as other features of the invention, are set forth in the disclosure which follows.

DETAILED DESCRIPTION OF PREFERRED EMBODIMENTS

EXAMPLE 1

A human testicular cDNA expression library was obtained, and screened with serum from a melanoma patient identified as MZ2. See e.g., parent application U.S. patent application Ser. No. 08/479,328 incorporated by reference now U.S. Pat. No. 5,698,896; also see U.S. patent application Ser. No. 08/725,182 also incorporated by reference; Sahin, et al., Proc. Natl. Acad. Sci. USA 92:11810–11813 (1995). This serum had been treated using the methodology described in these references. Briefly, serum was diluted 1:10, and then preabsorbed with transfected *E. coli* lysate. Following this preabsorption step, the absorbed serum was diluted 1:10, for a final dilution of 1:100. Following the final dilution the samples were incubated overnight at room temperature, with nitrocellulose membranes containing phage plaques prepared using the methodology referred to supra. The nitrocellulose membranes were washed, incubated with alkaline phosphatase conjugated goat anti-human $Fc_\gamma$ secondary antibodies, and the reaction was observed with the substrates 5-bromo-4-chloro-3-indolyl phosphate and nitroblue tetrazolium. In a secondary screen, any phagemids which encoded human immunoglobulin were eliminated.

A total of 3.6×105 pfus were screened, resulting in eight positive clones. Standard sequencing reactions were carried out, and the sequences were compared to sequence banks of known sequences.

Of the eight clones, two were found to code for known autoimmune disease associated molecules, i.e., Golgin-95 (Fritzler, et al., J. Exp. Med.178:49–62 (1993)), and human upstream binding factor (Chan, et al., J. Exp. Med. 174:1239–1244 (1991)). Three other clones were found to encode for proteins which are widely expressed in human tissue, i.e., ribosomal receptor, collagen type VI globular domain, and rapamycin binding protein. Of the remaining three sequences, one was found to be non-homologous to any known sequence, but was expressed ubiquitously in human tissues (this was found via RT-PCR analysis, but details are not provided herein). The remaining two were found to be identical to full length HOM-MEL-40, described in Ser. No. 08/479,328, while the eighth clone was found to be almost identical to "SSX3," as described by DeLeeuw, et al., Cytogenet. Cell Genet 73:179–183 (1996), differing therefrom in only two base pair differences in the coding region. These differences are probably artifactual in nature; however, the clone also included a 43 base pair 3'-untranslated region.

EXAMPLE 2

In order to carry out Southern blotting experiments, described infra, the SSX genes were amplified, using RT-PCR.

To do this, two primers were prepared using the published SSX2 sequence i.e.,

MEL-40A:

5'- CACACAGGAT CCATGAACGG AGA (SEQ ID NO: 3), and

MEL-40B:

5'- CACACAAAGC TTTGAGGGGA GTTACTCGTC ATC (SEQ. ID NO: 4) See Crew, et al., EMBO J 14:2333–2340 (1995). Amplification was then carried out using 0.25 U Taq polymerase in a 25 µl reaction volume, using an annealing temperature of 60° C. A total of 35 cycles were carried out.

EXAMPLE 3

The RT-PCR methodology described supra was carried out on testicular total RNA, and the amplification product was used in Southern blotting experiments.

Genomic DNA was extracted from non-neoplastic tissue samples, and then subjected to restriction enzyme digestion, using BamHI, Eco RI, or HindIII in separate experiments and then separated on a 0.7% agarose gel, followed by blotting onto nitrocellulose filters. The amplification products described supra were labeled with $^{32}P$, using well-known methods, and the labeled materials were then used as probes under high stringency conditions (65° C., aqueous buffer), followed by high stringency washes, ending with a final wash at 0.2×SSC, 0.2% SDS, 65° C.

The Southern blotting revealed more than 10 bands in each case (i.e., each of the BamHI, EcoRI, and HindIII digests), strongly suggesting that there is a family of SSX genes which contained more than the three identified previously. In view of this observation, an approach was designed which combined both PCR cloning, and restriction map analysis, to identify other SSX genes.

EXAMPLE 4

When the sequences of SSX1, 2 and 3 were compared, it was found that they shared highly conserved 5' and 3' regions, which explained why the olignucleotides of SEQ ID NOS: 3 and 4 were capable of amplifying all three sequences under the recited conditions, and suggested that this homology was shared by the family of SSX genes, whatever its size. Hence, the oligonucleotides of SEQ ID NOS: 3 and 4 would be sufficient to amplify the other members of the SSX gene family.

An analysis of the sequences of SSX1, 2 and 3 revealed that SSX1 and 2 contained a BglII site which was not shared by SSX3. Similarly, SSX3 contained an EcoRV site not shared by the other genes.

In view of this information, testicular cDNA was amplified, using SEQ ID NOS: 3 and 4, as described supra, and was then subjected to BglII digestion. Any BglII resistant sequences were then cloned, sequenced, and compared with the known sequences.

This resulted in the identification of two previously unidentified sequences, referred to hereafter as SSX4 and SSX5, presented as SEQ ID NOS: 5 and 6 herein. A search of the GenBank database found two clones, identified by Accession Number N24445 and W00507, both of which consisted of a sequence—tag—derived cDNA segment. The clone identified by N24445 contained the 3'-untranslated region of SSX4, and part of its coding sequence, while the one identified as W00507 contained a shorter fragment of the 3'-untranslated region of SSX4, and a longer part of the coding sequence. Specifically, N24445 consists of base 344 of SSX4 (SEQ ID NO:5), through the 3-end, plus 319 bases 3' of the stop codon. The W00507 sequence consists of a 99 base pair sequence, showing no homology to SSX genes followed by a region identical to nucleotides 280 through the end of SEQ ID NO:5, through 67 bases 3' of the stop codon of SEQ ID NO: 1.

Two forms of SSX4 (SEQ ID NO: 5) were identified. One of these lacked nucleotides 331 to 466 but was otherwise identical to SSX4 as presented in SEQ ID NO: 5. As is described infra, the shorter form is an alternatively spliced variant.

In Table 1, which follows, the nucleotide and amino acid sequences of the 5 known members of the SSX family are compared. One reads the table horizontally for nucleotide homology, and vertically for amino acid homology.

TABLE 1

Nucleotide and amino acid homology among SSX family members

| | Nucleotide Sequence Homology (%) | | | | |
|---|---|---|---|---|---|
| | SSX1 | SSX2 | SSX3 | SSX4 | SSX5 |
| SSX1 | | 89.1 | 89.6 | 89.4 | 88.7 |
| SSX2 | 78.2 | | 95.1 | 91.5 | 92.9 |
| SSX3 | 77.7 | 91.0 | | 91.1 | 92.7 |
| SSX4 | 79.3 | 79.8 | 80.9 | | 89.8 |
| SSX5 | 76.6 | 83.5 | 84.0 | 77.7 | |
| | Amino Acid Sequence Homology (%) | | | | |

Hence, SSX1 and SSX4 share 89.4% homology on the nucleotide level, and 79.3% homology on the amino acid level.

When the truncated form of SSX4 is analyzed, it has an amino acid sequence completely different from others, due to alternate splicing and shifting of a downstream open reading frame. The putative protein is 153 amino acids long, and the 42 carboxy terminal amino acids show no homology to the other SSX proteins.

EXAMPLE 5

The genomic organization of the SSX2 gene was then studied. To do this, a genomic human placental library (in lambda phage) was screened, using the same protocol and probes described supra in the discussion of the Southern blotting work. Any positive primary clones were purified, via two additional rounds of cloning.

Multiple positive clones were isolated, one of which was partially sequenced, and identified as the genomic clone of SSX2. A series of experiments carrying out standard subcloning and sequencing work followed, so as to define the exon—intron boundaries.

The analysis revealed that the SSX2 gene contains six exons, and spans at least 8 kilobases. All defined boundaries were found to observe the consensus sequence of exon/intron junctions, i.e. GT/AG.

The alternate splice variant of SSX4, discussed supra, was found to lack the fifth exon in the coding region. This was ascertained by comparing it to the SSX2 genomic clone, and drawing correlations therefrom.

EXAMPLE 6

The expression of individual SSX genes in normal and tumor tissues was then examined. This required the construction of specific primers, based upon the known sequences, and these follow, as SEQ ID NOS: 7–16:

TABLE 2

Gene-specific PCR primer sequences for individual SSX genes

| SSX1A (5'): | 5'-CTAAAGCATCAGAGAAGAGAAGC | [nt.44–66] |
|---|---|---|
| SSX1B (3'): | 5'-AGATCTCTTATTAATCTTCTCAGAAA | [nt.440–65] |
| SSX2A (5'): | 5'-GTGCTCAAATACCAGAGAAGATC | [nt.41–63] |
| SSX2B (3'): | 5'-TTTTGGGTCCAGATCTCTCGTG | .[nt.102–25] |
| SSX3A (5'): | 5'-GGAAGAGTGGGAAAAGATGAAAGT | [nt.454–75] |
| SSX3B (3'): | 5'-CCCCTTTTGGGTCCAGATATCA | [nt.458–79] |
| SSX4A (5'): | 5'-AAATCGTCTATGTGTATATGAAGCT | [nt.133–58] |
| SSX4B (3'): | 5'-GGGTCGCTGATCTCTTCATAAAC | [nt.526–48] |
| SSX5A (5'): | 5'-GTTCTCAAATACCACAGAAGATG | [nt.39–63] |
| SSX5B (3'): | 5'-CTCTGCTGGCTTCTCGGGCG | [nt.335–54] |

The specificity Of the clones was confirmed by amplifying the previously identified cDNA for SSX1 through SSX5. Taq polymerase was used, at 60° C. for SSX1 and 4, and 65° C. for SSX2, 3 and 5. Each set of primer pairs was found to be specific, except that the SSX2 primers were found to amplify minute (less than 1/20 of SSX2) amounts of SSX3 plasmid DNA.

Once the specificity was confirmed, the primers were used to analyze testicular mRNA, using the RT-PCR protocols set forth supra.

The expected PCR products were found in all 5 cases, and amplification with the SSX4 pair did result in two amplification products, which is consistent with alternative splice variants.

The expression of SSX genes in cultured melanocytes was then studied. RT-PCR was carried out, using the protocols set forth supra. No PCR product was found. Reamplification resulted in a small amount of SSX4 product, including both alternate forms, indicating that SSX4 expression in cultured melanocytes is inconsistent and is at very low levels when it occurs.

This analysis was then extended to a panel of twelve melanoma cell lines. These results are set forth in the following table.

TABLE 3

SSX expression in melanoma cell lines detected by RT-PCR*

|  | SSX1 | SSX2 | SSX3 | SSX4 | SSX5 |
|---|---|---|---|---|---|
| MZ2-Mel 2.2 | + | + | − | − | − |
| MZ2-Mel 3.1 | + | + | − | − | − |
| SK-MEL-13 | − | − | − | − | − |
| SK-MEL-19 | − | − | − | − | − |
| SK-MEL-23 | − | − | − | − | − |
| SK-MEL-29 | − | − | − | − | − |
| SK-MEL-30 | −* | −* | − | −* | − |
| SK-MEL-31 | − | − | − | − | − |
| SK-MEL-33 | − | − | − | − | − |
| SK-MEL-37 | + | + | − | + | + |
| SK-MEL-179 | − | − | − | − | − |
| M24-MET | − | − | − | − | − |

*Positive (+) denotes strong expression. Weak positivity was observed inconsistently in SK-MEL-30 for SSX 1,2, and 4, likely representing low level expression.

EXAMPLE 7

Additional experiments were carried out to analyze expression of the members of the SSX family in various tumors. To do this, total cellular RNA was extracted from frozen tissue specimens using guanidium isothiocyanate for denaturation followed by acidic phenol extraction and isopropanol precipitation, as described by Chomczynski, et al, Ann. Biochem 162: 156–159 (1987), incorporated by reference. Samples of total RNA (4 ug) were primed with oligodT(18) primers, and reverse transcribed, following standard methodologies. The integrity of the cDNA thus obtained was tested via amplifying B-actin transcripts in a 25 cycle, standard PCR, as described by Tureci, et al, Canc. Res. 56: 4766–4772 (1996).

In order to carry out PCR analyses, the primers listed as SEQ ID NOS: 5–14, supra were used, as well as SEQ ID NOS: 17 and 18, i.e.:

ACAGCATTAC CAAGGACAGC AGCCACC

GCCAACAGCA AGATGCATAC CAGGGAC

These two sequences were each used with both SEQ ID NOS: 6 and 8 in order to detect the SYT/SSX fusion transcript reported for synovial sarcoma by Clark et al, supra, and Crew, et al, supra. The amplification was carried out by amplifying 1 μl of first strand cDNA with 10 pMol of each dNTP, and 1.67 mN MgCl$_2$ in a 30 μl reaction. Following 12 minutes at 94° C. to activate the enzyme, 35 cycles of PCR were performed. Each cycle consisted of 1 minute for annealing (56° C. for SEQ ID NOS: 7 & 8; 67° C. for SEQ ID NOS: 9 & 10; 65° C. for SEQ ID NOS: 11 & 12; 60° C. for SEQ ID NOS: 13 & 14; 66° C. for SEQ ID NOS: 15 & 16; 60° C. for SEQ ID NOS: 17 & 8 and 18 & 10), followed by 2 minutes at 72° C., 1 minute at 94° C., and a final elongation step at 72° C. for 8 minutes. A 15 ye aliquot of each reaction was size fractionated on a 2% agarose gel, visualized with ethidium bromide staining, and assessed for expected size. The expected sizes were 421 base pairs for SEQ ID NOS: 7 & 8; 435 base pairs for SEQ ID NOS: 9 & 10; 381 base pairs for SEQ ID NOS: 11 & 12; 413 base pairs for SEQ ID NOS: 13 & 14, and 324 base pair for SEQ ID NOS: 15 & 16. The conditions chosen were stringent, so as to prevent crossannealing of primers to other members of the SSX family. Additional steps were also taken to ensure that the RT-PCR products were derived from cDNA, and not contaminating DNA. Each experiment was done in triplicate. A total of 325 tumor specimens were analyzed. The results are presented in Tables 4 & 5 which follow.

It is to be noted that while most of the SSX positive tumors expressed only one member of the SSX family, several tumor types showed coexpression of two or more genes.

Expression of SSX genes in synovial sarcoma was analyzed, because the literature reports that all synovial sarcoma cases analyzed have been shown to carry either the SYT/SSX1 or SYT/SSX2 translocation, at breakpoints flanked by the primer sets discussed herein, i.e., SEQ ID NO: 17/SEQ ID NO: 8; SEQ ID NO: 17/SEQ ID NO: 10; SEQ ID NO. 17/SEQ ID NO: 8; SEQ ID NO: 18/SEQ ID NO: 10. The PCR work described supra showed that SYT/SSX1 translocations were found in three of the synovial sarcoma samples tested, while SYT/SSX2 was found in one. The one in which it was found was also one in which SYT/SSX1 was found. Expression of SSX appeared to be independent of translocation.

TABLE 4

Expression of SSX genes by human neoplasms

| Tumor entity | Tissues tested | SSX1 | SSX2 | SSX3 | SSX4 | SSX5 | at lease one positive | % |
|---|---|---|---|---|---|---|---|---|
| Lymphoma | 11 | — | 4 | — | — | — | 4 | 36 |
| Breast cancer | 67 | 5 | 5 | — | 10 | — | 16 | 23 |
| Endometrial cancer | 8 | 1 | 2 | — | 1 | 1 | 1 | 13 |
| Colorectal cancer | 58 | 3 | 7 | — | 9 | 1 | 16 | 27 |
| Ovarian cancer | 12 | — | — | — | 6 | — | 6 | 50 |
| Renal cell cancer | 22 | — | 1 | — | — | — | 1 | 4 |
| Malignant melanoma | 37 | 10 | 13 | — | 10 | 2 | 16 | 43 |
| Glioma | 31 | — | 2 | — | 3 | — | 5 | 16 |
| Lung cancer | 24 | 1 | 4 | — | 1 | 1 | 5 | 21 |
| Stomach cancer | 3 | — | — | — | 1 | — | 1 | 33 |
| Prostatic cancer | 5 | — | 2 | — | — | — | 2 | 40 |
| Bladder cancer | 9 | 2 | 4 | — | 2 | — | 5 | 55 |
| Head-Neck cancer | 14 | 3 | 5 | — | 4 | 1 | 8 | 57 |
| Synovial sarcoma | 4 | — | 2 | — | 1 | 1 | 3 | 75 |
| Leukemia | 23 | — | — | — | — | — | 0 | 0 |
| Leiomyosarcoma | 6 | — | — | — | — | — | 0 | 0 |
| Thyroid cancer | 4 | — | — | — | — | — | 0 | 0 |
| Seminoma | 2 | — | — | — | — | — | 0 | 0 |
| Total | 325 | 25 | 50 | 0 | 48 | 7 | 89 | |

TABLE 5

Expression pattern of individual SSX genes in SSX-positive tumor samples.[1]

|  | SSX1 | SSX2 | SSX4 | SSX5 |
|---|---|---|---|---|
| Breast Cancer (67 specimens) | | | | |
| 51 specimens | − | − | − | − |
| 7 specimens | − | − | + | − |

TABLE 5-continued

Expression pattern of individual SSX genes in SSX-positive tumor samples.[1]

| | | | | |
|---|---|---|---|---|
| 4 specimens | − | + | − | − |
| 2 specimens | + | − | − | − |
| 2 specimens | + | − | + | − |
| 1 specimen | + | + | + | − |
| Melanoma (37 specimens) | | | | |
| 21 specimens | − | − | − | − |
| 5 specimens | + | + | + | − |
| 4 specimens | − | + | − | − |
| 2 specimens | − | + | + | − |
| 1 specimen | + | − | − | − |
| 1 specimen | + | + | − | − |
| 1 specimen | + | − | + | − |
| 1 specimen | + | − | + | + |
| 1 specimen | + | + | + | + |
| Endomet. Cancer (8 specimens) | | | | |
| 7 specimens | − | − | − | − |
| 1 specimen | + | + | + | + |
| Glioma (31 specimens) | | | | |
| 25 specimens | − | − | − | − |
| 3 specimens | − | + | − | − |
| 2 specimens | − | − | + | − |
| Lung Cancer (24 specimens) | | | | |
| 19 specimens | − | − | − | − |
| 3 specimens | − | + | − | − |
| 1 specimen | − | − | − | + |
| 1 specimen | + | + | + | − |
| Colorectal Cancer (58 specimens) | | | | |
| 42 specimens | − | − | − | − |
| 7 specimens | − | + | − | − |
| 5 specimens | − | − | + | − |
| 3 specimens | + | − | + | − |
| 1 specimen | − | − | + | + |
| Bladder Cancer (9 specimens) | | | | |
| 4 specimens | − | − | − | − |
| 2 specimens | − | + | − | − |
| 1 specimen | − | − | + | − |
| 1 specimen | + | + | − | − |
| 1 specimen | + | + | + | − |
| Head-Neck Cancer (14 specimens) | | | | |
| 6 specimens | − | − | − | − |
| 2 specimens | + | − | − | − |
| 2 specimens | − | + | + | − |
| 1 specimen | − | + | − | − |
| 1 specimen | − | − | + | − |
| 1 specimen | + | + | − | − |
| 1 specimen | − | + | + | + |

| Synovial Sarcoma (4 specimens) | SSX1 | SSX2 | SSX4 | SSX5 | SYT/SSX1 | SYT/SSX5 |
|---|---|---|---|---|---|---|
| Sy1 | − | − | + | − | + | − |
| Sy2 | − | + | − | + | + | − |
| Sy3 | − | − | − | − | − | + |
| Sy4 | − | + | − | − | + | − |

EXAMPLE 8

The amino acid sequence of the proteins encoded by the SS genes were analyzed for peptide sequences which correspond to HLA binding motifs. This was done using the algorithm taught by Parker et al., J. Immunol. 142: 163 (1994), incorporated by reference. In the information which follows, the amino acid sequence, the HLA molecule to which it presumably binds, and the positions in the relevant SS molecule are given. The resulting complexes should provoke a cytolytic T cell response. This could be determined by one skilled in the art following methods taught by, e.g., van der Bruggen, et al., J. Eur. J. Immunol. 24: 3038–3043 (1994), incorporated by reference.

| | | | | SEQ ID NO: |
|---|---|---|---|---|
| SSX-5 | | | | |
| A2 | KASEKIIYV | 41–49 | | 19 |
| A3 | GTFPKITPEK | 106–115 | | 20 |
| | KLNTSEVNK | 144–153 | | 21 |
| A24 | KYEAMTKLGF | 54–63 | | 22 |
| B7 | HPQMTFGRL | 96–104 | | 23 |
| | GPQNNGKQL | 131–139 | | 24 |
| B8 | RVRERKQL | 167–174 | | 25 |
| B44 | YEAMTKLGF | 55–63 | | 26 |
| | RERKQLVIY | 169–177 | | 27 |
| B52 | KQLVIYEEJ | 172–180 | | 28 |
| | MTFGRLQGIF | 99–108 | | 29 |
| SSX-4 | | | | |
| A2 | KSSEKJVYV | 41–49 | | 30 |
| | VMTKLGFKV | 57–65 | | 31 |
| | YVYMKLNYEV | 48–57 | | 32 |
| | KLNYEVMTKL | 52–61 | | 33 |
| A3 | KLNYEVMTK | 52–60 | | 34 |
| A24 | NYEVMTKLGF | 54–63 | | 35 |
| B7 | RPQMTFGSL | 96–104 | | 36 |
| | KPAEEENGL | 115–123 | | 37 |
| | GPQNDGKQL | 131–139 | | 38 |
| | CPPGNPSTL | 140–148 | | 39 |
| B8 | RLRERKQL | 167–174 | | 40 |
| B35 | RPRDDAQI | 10–17 | | 41 |
| | KPAEEENGL | 115–123 | | 42 |
| B44 | YEVMTKLGF | 55–63 | | 43 |
| | RERKQLVVY | 169–177 | | 44 |
| B52 | KQLVVYEEI | 172–180 | | 45 |
| | MTFGSLQRJF | 99–108 | | 46 |
| SSX-2 | | | | |
| A2 | KIQKAFDDI | 20–28 | | 47 |
| | KASEKIFYV | 41–49 | | 48 |
| | AMTKLGFKA | 57–65 | | 49 |
| | RLQGJSPKJ | 103–111 | | 50 |
| | RLRERKQLV | 167–175 | | 51 |
| A3 | TLPPFMCNK | 66–74 | | 52 |
| | KIFYVYMKRK | 45–54 | | 53 |
| A24 | KYEAMTKLGF | 54–63 | | 54 |
| B7 | RPQMTFGRL | 96–104 | | 55 |
| | GPQNDGKEL | 131–139 | | 56 |
| B8 | RLRBRKQL | 167–174 | | 57 |
| B35 | FSKBBWEKM | 32–40 | | 58 |
| B44 | YEAMTKLGF | 55–63 | | 59 |
| | RERKQLVIY | 169–177 | | 60 |
| B52 | LQGISPKIM | 104–190 | | 61 |
| | KQLVIYEEI | 172–180 | | 62 |
| SSX-1 | | | | |
| A2 | AMTKLGEKV | 57–65 | | 63 |
| | AMTKLGFKV | 56–65 | | 64 |
| A3 | TLPPFMCNK | 66–74 | | 65 |
| A24 | NYKAMTKLGF | 54–63 | | 66 |
| B7 | HPQMTFGRL | 96–104 | | 67 |
| | GPQNDGKOL | 131–139 | | 68 |
| B8 | RLRERKQL | 167–174 | | 69 |
| B44 | RERKQLVIY | 169–177 | | 70 |
| B52 | KQLVIYEEI | 172–180 | | 71 |
| | MTFGRLHRRII | 99–108 | | 72 |

The foregoing examples describe the isolation and cloning of nucleic acid molecules for the SSX4, splice variant of SSX4, and SSX5 genes as well as methods for determining expression of the various SSX genes as a possible indication of cancer. As was indicated, supra, these genes are expressed in tumor cells, thereby enabling the skilled artisan to utilize these for, e.g., assaying for cancer. The determination of expression can be carried out via, e.g., determination of transcripts of an SSX gene or genes, via nucleic acid hybridization, such as via polymerase chain reaction. In a preferred embodiment, one determines presence of a transcript of an SSX gene by contacting a sample with a nucleic acid molecule which specifically hybridizes to the transcript.

The hybridization of the nucleic acid molecule to a target is indicative of expression of an SSX gene, and of the possibility of cancer. Preferably, this is done with two primer molecules, as in a polymerase chain reaction. Determination of expression of more than one SSX gene in the context of these assays also is a part of the invention. For the convenience of the artisan, the nucleotide sequences of SSX1 and SSX2, which are known, are presented herein as SEQ ID NOS: 1 & 2.

Alternate assays are also a part of the invention. Members of the CT family are known to provoke antibodies in the individual who expresses a CT family member. Hence, one can carry out the assays described herein via, e.g., determining antibodies in a sample taken from a subject in question Most preferably, the sample being analyzed is serum. Such assays can be carried out in any of the standard ways one determines antibodies, such as by contacting the sample with an amount of protein or proteins, and any additional reagents necessary to determine whether or not the antibody binds. One approach involves the use of immobilized protein, where the protein is immobilized in any of the standard ways known to the art, followed by contact with the sample and then, e.g., anti-IgG, anti-Fc antibodies, and so forth. Conversely, presence of an SSX protein can also be determined, using antibodies in the place of the proteins of the above described assays.

The correlation of SSX expression with cancer also suggests various therapeutic methods and compositions useful in treating conditions associated with abnormal SSX expression. "Abnormal SSX expression" in this context may mean expression per se, or levels which differ from those in a normal individual, i.e., they may be lower or higher.

The invention envisions therapeutic approaches such as the use of antisense molecules to inhibit or block expression. This antisense molecules are oligonucleotides which hybridize to the nucleic acid molecules and inhibit their expression. Preferably these are 17–50 nucleotides in length. These antisense oligonucleotides are preferably administered in combination with a suitable carrier, such as a cationic liposome.

Other therapeutic approaches include the administration of SSX proteins per se, one or more antigenic peptides derived therefrom, as well as so-called polytopic vaccines. These include a plurality of antigenic peptides, untied together, preferably by linker sequences. The resulting peptides may bind to either MHC-Class I or Class II molecules. These proteins, peptides, or polytopic vaccines may be administered in combination with an appropriate adjuvant. They may also be administered in the form of genetic constructs which are designed to permit expression of the protein, the peptide, the polytopic structures, etc. Peptides and polytopic structures can be expressed by so-called "minigenes" i.e., DNA molecules designed to express portions of the entire SSX molecule, or the various portions of the molecules, linked together as described supra. One can formulate the therapeutic compositions and approaches described herein such that one, or more than one SSX protein, is used as the source of the compositions. In other words, if a whole protein approach is used, one SSX molecule may be used, or two or more may be combined in one formulation. For peptides, these can all be taken from one SSX molecule, or be combinations of peptides taken from more than one. The polytopic structures described herein can also be made up of components of one, or more than one, SSX molecule.

The amount of agent administered and the manner in which it is administered will vary, based on the condition being treated and the individual. Standard forms of administration, such as intravenous, intradermal, subcutaneous, oral, rectal and transdermal administration can be used. With respect to formulations, the proteins and or peptides may be combined with adjuvant and/or carriers such as a saponin, GM-CSF, one or more interleukin, an emulsifying oil such as vitamin E, one or more heat shock protein, etc.

When the nucleic acid approach is utilized, various vectors, such as Vaccinia or adenovirus based vectors can be used. Any vector useful in eukaryotic transfection, such as in transfection of human cells, can be used. These vectors can be used to produce, e.g., cells such as dendritic cells which present relevant peptide/MHC complexes on their surface. The cells can then be rendered non-proliferative prior to their administration, using standard methodologies.

Other aspects of the invention will be clear to the skilled artisan and need not be reiterated herein.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

What is claimed is:

1. A method for determining presence of cancer which is neither melanoma nor synovial sarcoma in a subject, comprising assaying a sample taken from said subject to determine expression of an SSX gene selected from the group consisting of SSX1, SSX4 and SSX5, wherein expression of said SSX gene is indicative of cancer which is neither melanoma nor synovial sarcoma in said subject.

2. The method of claim 1, wherein said SSX gene is SSX1.

3. The method of claim 2, wherein said cancer is breast cancer, endometrial cancer, colorectal cancer, lung cancer, bladder cancer, or head-neck cancer.

4. The method of claim 1, wherein said cancer is lymphoma, breast cancer, endometrial cancer, colorectal cancer, renal cell cancer, glioma, lung cancer, prostate cancer, bladder cancer, or head-neck cancer.

5. The method of claim 1, wherein said SSX gene is SSX4.

6. The method of claim 5, wherein said cancer is breast cancer, endometrial cancer, colorectal cancer, ovarian cancer, glioma, lung cancer, stomach cancer, bladder cancer, or head-neck cancer.

7. The method of claim 1, wherein said SSX gene is SSX5.

8. The method of claim 7, wherein said cancer is endometrial cancer, colorectal cancer, lung cancer, or head-neck cancer.

9. The method of claim 1, comprising contacting said sample with at least two nucleic acid molecules, each of which hybridizes specifically to a different SSX gene.

10. The method of claim 9, wherein said cancer is breast cancer.

11. The method of claim 9, wherein said cancer is endometrial cancer.

12. The method of claim 9, wherein said cancer is lung cancer.

13. The method of claim 9, wherein said cancer is colorectal cancer.

14. The method of claim 9, wherein said cancer is bladder cancer.

15. The method of claim 9, wherein said cancer is head-neck cancer.

16. The method of claim 1, comprising determining expression by contacting said sample with a nucleic acid molecule which specifically hybridizes to said SSX gene, and determining hybridization as a determination of possible presence of cancer in said sample.

17. The method of claim 16, comprising polymerase chain reaction.

18. The method of claim 1, comprising determining antibodies which specifically bind to said SSX protein in said sample.

19. The method of claim 18, wherein said sample is serum.

20. The method of claim 1, comprising determining an SSX protein expressed by said SSX gene.

21. A method for determining presence of cancer selected from the group consisting of endometrial cancer, bladder cancer, and head and neck cancer in a subject believed to suffer from said cancer, comprising assaying a sample taken from said subject to determine expression of SSX2, wherein expression of SSX2 is indicative of presence of said cancer.

* * * * *

UNITED STATES PATENT AND TRADEMARK OFFICE
CERTIFICATE OF CORRECTION

PATENT NO. : 6,287,756 B1  Page 1 of 1
APPLICATION NO. : 09/105839
DATED : September 11, 2001
INVENTOR(S) : Tureci Ozlem et al.

It is certified that error appears in the above-identified patent and that said Letters Patent is hereby corrected as shown below:

Title page, Item (63) continuation-in-part of application No. 08/851,130, filed on May 5, 1997, now Pat. No. 5,779,359. Correction: should be Patent No. 6,291,658.

Signed and Sealed this

Seventh Day of September, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 6,287,756 B1 | Page 1 of 1 |
| APPLICATION NO. | : 09/105839 | |
| DATED | : September 11, 2001 | |
| INVENTOR(S) | : Tureci Ozlem et al. | |

It is certified that error appears in the above-identified patent and that said Letters Patent is hereby corrected as shown below:

Title page, Item (63) continuation-in-part of application No. 08/851,138, filed on May 5, 1997, now Pat. No. 5,779,359. Correction: should be Patent No. 6,291,658.

This certificate supersedes the Certificate of Correction issued September 7, 2010.

Signed and Sealed this
Fourth Day of September, 2012

David J. Kappos
*Director of the United States Patent and Trademark Office*